(12) United States Patent
Guena et al.

(10) Patent No.: US 10,487,033 B2
(45) Date of Patent: Nov. 26, 2019

(54) BATTERY WITH VARIABLE ELECTROCHEMICAL CELLS CONFIGURATION

(71) Applicant: Blue Solutions Canada Inc., Boucherville (CA)

(72) Inventors: Thierry Guena, Longueuil (CA); Cedric Reboul-Salze, Montreal (CA); Patrick Leblanc, Boucherville (CA); Frederic Cotton, Montreal (CA); Alain Vallee, Varennes (CA)

(73) Assignee: BLUE SOLUTIONS CANADA INC., Boucherville (CA)

( * ) Notice: Subject to any disclaimer, the term of this patent is extended or adjusted under 35 U.S.C. 154(b) by 204 days.

(21) Appl. No.: 15/375,114

(22) Filed: Dec. 11, 2016

(65) Prior Publication Data

US 2017/0179553 A1 Jun. 22, 2017

Related U.S. Application Data

(60) Provisional application No. 62/266,036, filed on Dec. 11, 2015.

(51) Int. Cl.
| | |
|---|---|
| *C07C 37/20* | (2006.01) |
| *H01M 10/6551* | (2014.01) |
| *H01M 10/613* | (2014.01) |
| *H01M 10/052* | (2010.01) |
| *H01M 2/10* | (2006.01) |

(Continued)

(52) U.S. Cl.
CPC .............. *C07C 37/20* (2013.01); *C07C 39/16* (2013.01); *H01M 2/1077* (2013.01);
(Continued)

(58) Field of Classification Search
CPC ............ H01M 10/613; H01M 10/6551; H01M 10/052; H01M 10/0525; H01M 10/0565; H01M 10/0587; H01M 2/1077
See application file for complete search history.

(56) References Cited

U.S. PATENT DOCUMENTS 8,729,860 B2   5/2014   Dellantoni et al.
8,795,875 B2   8/2014   Lee et al.
(Continued)

FOREIGN PATENT DOCUMENTS

| JP | 2014303456 | 10/2004 |
| JP | 2010170942 | 5/2010 |
| JP | 2012160283 | 8/2012 |

OTHER PUBLICATIONS

International Search Report dated Mar. 6, 2017 in International application No. PCT/CA2016/000312.
(Continued)

*Primary Examiner* — Jimmy Vo
(74) *Attorney, Agent, or Firm* — BCF LLP (57) ABSTRACT

A lithium battery comprising a plurality of electrochemical cells assembled together and a rigid casing forming an enclosure. The plurality of electrochemical cells includes: at least one first electrochemical cell, at least one second electrochemical cell; and at least one third electrochemical cell disposed between the at least one first electrochemical cell and the at least one second electrochemical cell. The at least one first electrochemical cell is disposed between a first wall of the casing and the at least one third electrochemical cell. The at least one second electrochemical cell is disposed between a second wall of the casing and the at least one third electrochemical cell. The first and second walls provide a heat sink path to dissipate excess heat generated by the plurality of electrochemical cells. The at least one first and second electrochemical cells are more capacitive than the at least one third electrochemical cell.

15 Claims, 8 Drawing Sheets

(51) Int. Cl.
*H01M 10/0525* (2010.01)
*H01M 10/0565* (2010.01)
*H01M 10/0587* (2010.01)
*C07C 39/16* (2006.01)
*H01M 10/6556* (2014.01)

(52) U.S. Cl.
CPC ..... *H01M 10/052* (2013.01); *H01M 10/0525* (2013.01); *H01M 10/0565* (2013.01); *H01M 10/0587* (2013.01); *H01M 10/613* (2015.04); *H01M 10/6551* (2015.04); *H01M 10/6556* (2015.04); *C07C 2527/03* (2013.01); *H01M 2300/0065* (2013.01); *Y02T 10/7011* (2013.01)

(56) References Cited

U.S. PATENT DOCUMENTS

| | | |
|---|---|---|
| 8,828,584 B2 | 9/2014 | Gunji et al. |
| 10,224,578 B2 | 3/2019 | Cotton et al. |
| 2002/0028380 A1* | 3/2002 | Tanjo .................... H01M 4/131 429/209 |
| 2011/0213509 A1 | 9/2011 | Onnerud et al. |
| 2013/0236768 A1 | 9/2013 | Park et al. |
| 2014/0197794 A1 | 7/2014 | Gu et al. |
| 2014/0199570 A1 | 7/2014 | Cho |
| 2014/0322583 A1* | 10/2014 | Choi .................... B60L 3/0046 429/120 |
| 2015/0204948 A1 | 7/2015 | Karoui et al. |
| 2017/0179553 A1 | 6/2017 | Guena et al. |

OTHER PUBLICATIONS

Espacenet, English translation of the abstract of JP 200403456A.
Espacenet, English translation of the abstract of JP 2010170942A.
Espacenet, English translation of the abstract of JP 2012160283A.

\* cited by examiner

BATTERY WITH VARIABLE ELECTROCHEMICAL CELLS CONFIGURATION

CROSS REFERENCE

This application claims priority from U.S. 62/266,036, the contents of which are incorporated herein by reference.

FIELD OF THE INVENTION

The present invention relates to a lithium polymer battery operating at temperatures and more specifically to a battery having electrochemical cells configurations adapted to manage these operating temperatures.

BACKGROUND OF THE INVENTION

Lithium polymer batteries are typically built as large format batteries of 20 kWh or more for use in electric vehicle, in stationary applications for back-up to ensure continuity to applications that cannot afford a grid power outage such as telecommunication stations, data centers, etc., or to provide alternate power source for peak shaving purposes in industrial or residential buildings.

Lithium polymer batteries consist of a plurality of electrochemical cells connected in series enclosed in a rigid casing which protect the electrochemical cells. Each electrochemical cell includes a plurality of elementary cell laminates connected in parallel. Each laminate includes an anode or negative electrode, a cathode or positive electrode, and a solid electrolyte comprising a polymer and a lithium salt separating the positive electrode from the negative electrode and providing ionic conductivity between the electrodes. The negative electrode may be a lithium or lithium alloy metal sheet or an active material capable of insertion and de-insertion of lithium ions such as carbon or $Li_4Ti_5O_{12}$ in a polymer binder while the positive electrode consists of electrochemically active material particles such as $LiFePO_4$, $LiMnO_2$, $LiMn_2O_4$, etc., an electronically conductive additive and a solid polymer electrolyte which acts as a binder as well as provides the required ionic path between the electrochemically active material particles of the positive electrode and the solid electrolyte separator.

Contrary to lithium ion batteries which use a liquid electrolyte, lithium polymer batteries uses a solid electrolyte rendering this technology extremely safe. However, to obtain optimal ionic conductivity and therefore optimal performance, the electrochemical cells must be heated to temperatures of 60° C. to 80° C. Lithium polymer batteries therefore include a heating system to maintain the battery at a nominal temperature of 40° C. and to rapidly raise the temperature of the electrochemical cells to between 60° C. and 80° C. at the beginning of their discharge mode to obtain optimal performance from the battery. Once the optimal temperature is reached, the discharge operation generates sufficient heat to maintain the battery at its optimal temperature.

In operation, the excess heat generated by the plurality of electrochemical cells making up the battery is dissipated through the walls of the battery casing. The battery casing is preferably made of a rigid and heat conductive material such as aluminum or alloy thereof that efficiently conducts the excess heat outside the battery casing and there may be a cooling system outside the battery casing to accelerate heat dissipation when require.

In normal discharge operation, it was found that in a stack of electrochemical cells encased in a battery casing as described above, the electrochemical cells located adjacent to the walls of the battery casing were the first to reach their end of discharge voltage thereby marginally lowering the overall discharge capacity of the battery. This phenomena was attributed to the fact that these particular electrochemical cells were operating at slightly lower operating temperatures because they were losing heat more rapidly through the walls of the battery casing than the other electrochemical cells located farther away from the walls of the battery casing Thus, there is a need for a battery casing and electrochemical cells configurations adapted to compensate for heat loss through heat sinks of the battery casing.

SUMMARY OF THE INVENTION

It is an object of the present invention to ameliorate at least some of the inconveniences present in the prior art.

In one aspect, the invention provides a lithium battery comprising a plurality of electrochemical cells assembled together which are inserted in a rigid casing having side walls and upper and lower walls forming an enclosure; and at least one heat sink path to dissipate excess heat generated by the electrochemical cells; the electrochemical cells are assembled such that the electrochemical cells positioned adjacent to the heat sink path have a different configuration than the other electrochemical cells of the battery.

In a further aspect, the electrochemical cells positioned adjacent to the heat sink path are more capacitive than the other electrochemical cells of the bundle.

In a further aspect, the more capacitive electrochemical cells include at least n+1 laminates.

In a another aspect, the invention provides a rigid casing further comprises a internal wall providing a further heat sink path and wherein the electrochemical cells positioned adjacent to the internal wall have a different configuration than the other electrochemical cells of the bundle.

In another aspect, the electrochemical cells positioned adjacent to the heat sink path have a lower impedance than the other electrochemical cells of the battery.

In another aspect, the electrochemical cells positioned adjacent to the heat sink path include laminates in which the cathode is thinner than the other electrochemical cells of the bundle.

Embodiments of the present invention each have at least one of the above-mentioned objects and/or aspects, but do not necessarily have all of them. It should be understood that some aspects of the present invention that have resulted from attempting to attain the above-mentioned objects may not satisfy these objects and/or may satisfy other objects not specifically recited herein.

Additional and/or alternative features, aspects, and advantages of embodiments of the present invention will become apparent from the following description, the accompanying drawings, and the appended claims.

BRIEF DESCRIPTION OF THE DRAWINGS

For a better understanding of the present invention, as well as other aspects and further features thereof, reference is made to the following description which is to be used in conjunction with the accompanying drawings, where.

DETAILED DESCRIPTION OF THE PREFERRED EMBODIMENTS

Figure 1:
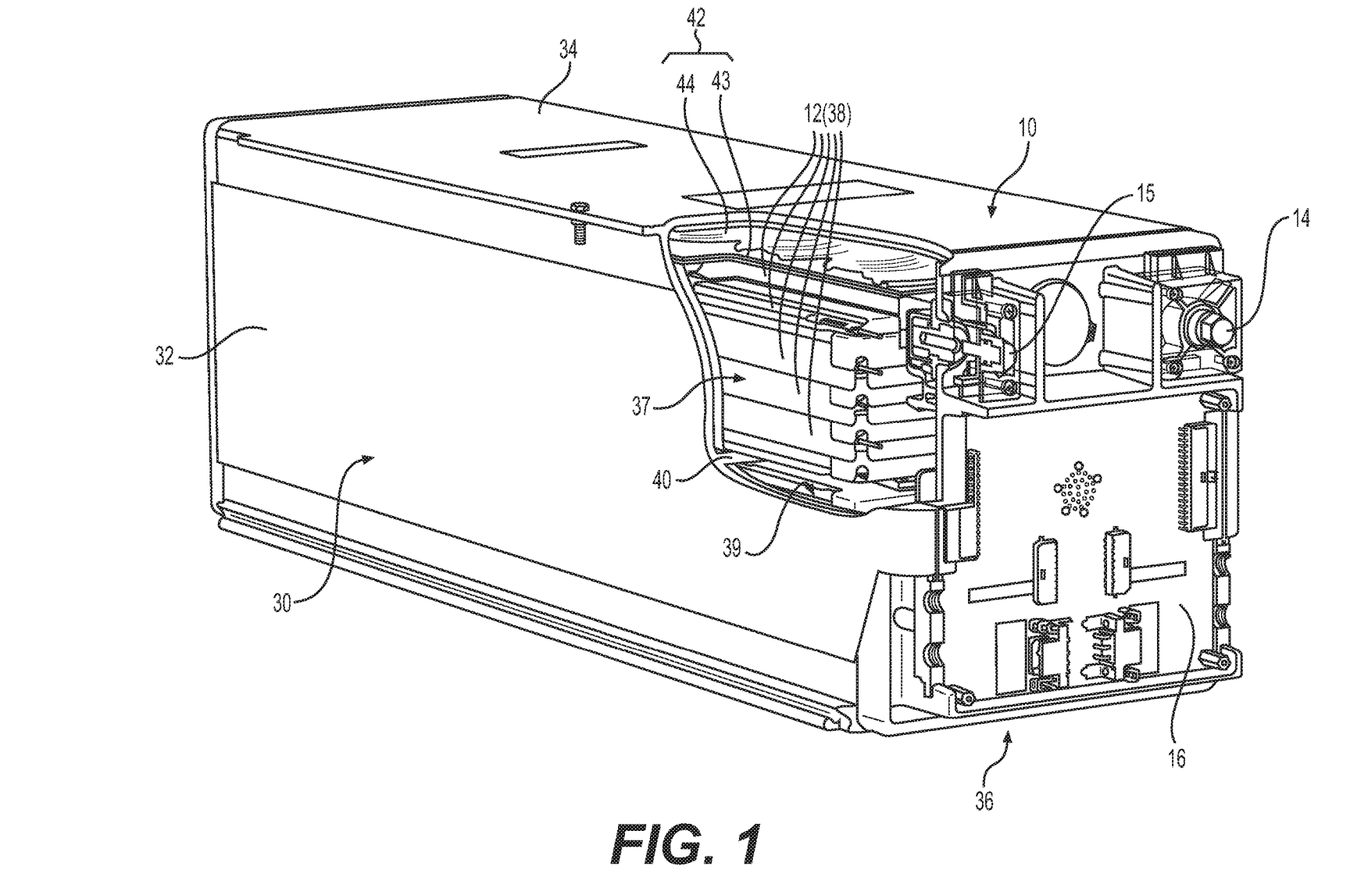
FIG. 1 is a perspective view of an example of a battery comprising a plurality of electrochemical cells.

FIG. 1 illustrates one embodiment of a lithium metal polymer battery 10, with a cut-away portion showing its internal components. In this specific example, the battery 10 includes a plurality of electrochemical cells 12 stacked one against the other, connected together in series and connected to battery poles 14 and 15. The stack of electrochemical cells 12 is connected to an electronic control board 16 that controls the charge and discharge mode of the electrochemical cells 12 and monitors various parameters of the battery 10 including the tension or voltage of each individual electrochemical cell 12 at all-time as well as the temperature of the battery 10.

The battery 10 includes a rigid casing 30 made of extruded aluminum having side walls 32 and upper and lower walls 34 forming an enclosure 37. The stack of electrochemical cells 12 are assembled together to form a bundle 38 which is inserted into the enclosure 37 formed by the rigid casing 30 for protection and for thermally isolating the bundle 38 to maintain optimal temperatures of the electrochemical cells 12. In the illustrated embodiment of FIG. 1, the rigid casing 30 further comprises a internal wall 40 extending the entire length of the rigid casing 30 providing added rigidity the casing 30 and thereby forming two distinct enclosures 37 and 39 such that the battery 10 includes two bundles 38 of electrochemical cells 12, one inserted in each enclosure 37 and 39. Each bundle 38 is maintained under pressure by a pressure system 42 consisting of a series of springs 44 exerting a force on a plate 43 which applies an even pressure on the bundle 38.

The battery 10 includes a heating system (not shown) located along the side walls 32 of the rigid casing 30. The heating system provides heat to the bundles 37 and 39 through the side walls 32 of the rigid casing 30 to maintain the battery 10 at a nominal temperature of 40° C. in floating mode and to rapidly raise the temperature of the electrochemical cells 12 to between 60° C. and 80° C. at the beginning of their discharge mode.

Once the discharge temperature has been reached, the upper and lower walls 34 and 36 and the internal wall 40 of the rigid casing 30 provide a heat sink path to dissipate excess heat generated by the bundles 38 of electrochemical cells 12 in order to prevent overheating of the electrochemical cells 12.

Figure 2:
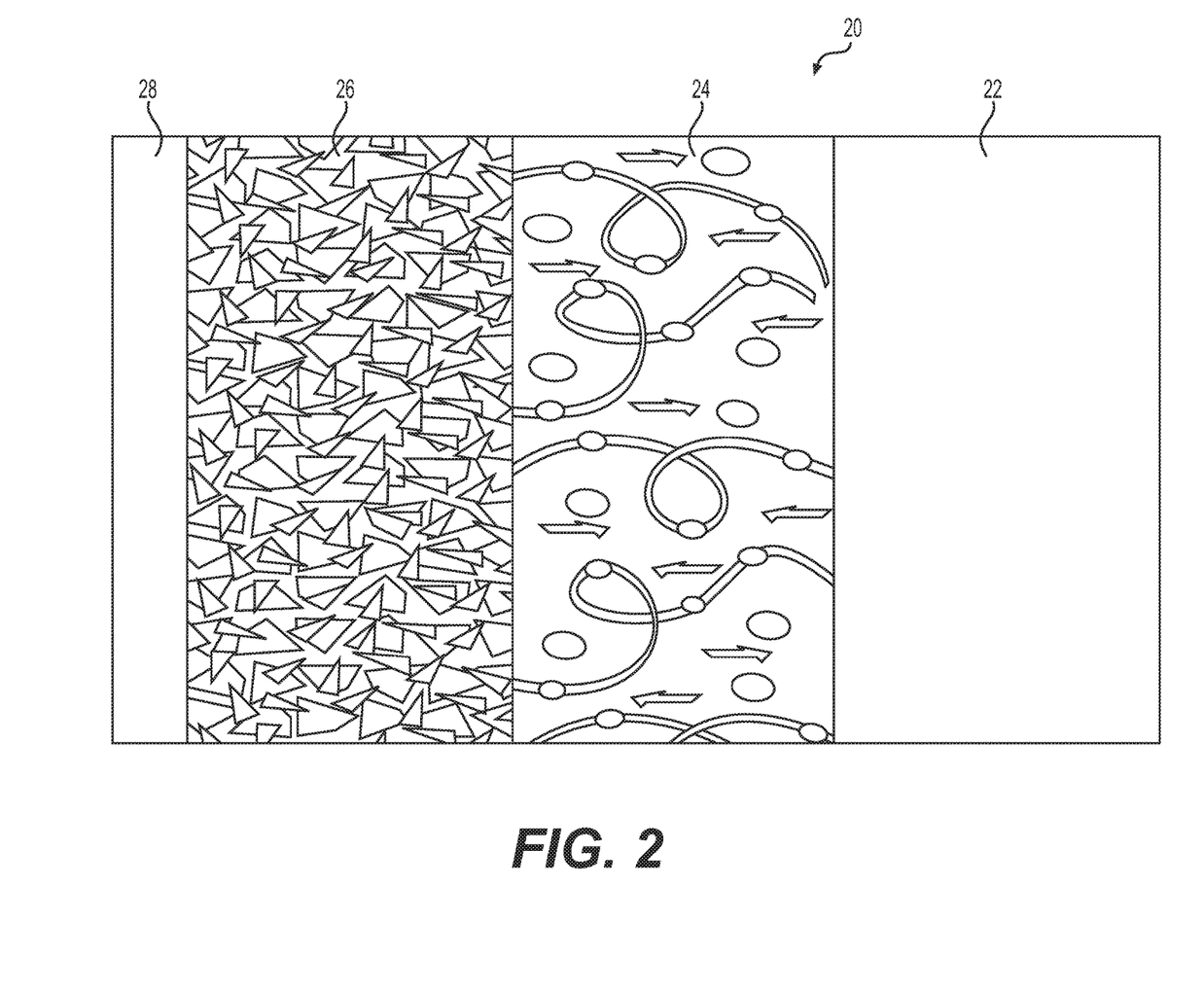
FIG. 2 is a schematic view of a single electrochemical cell laminate.

Each electrochemical cell 12 consists of a multi-layer assembly of single laminates 20 as illustrated schematically in FIG. 2. Each laminate 20 comprises an anode 22 that acts as a lithium source, a cathode 26 having an electrochemically active material capable of occluding and releasing lithium ions and an electrolyte 24 separating the anode 22 from the cathode 26 and acting as a lithium ion carrier. The anode 22 and the cathode 26 are made of materials capable of reversible insertion of lithium ions. The anode 22 may be a metallic lithium foil or a composite material comprising, for example, carbon-based intercalation compounds and a polymer, copolymer or terpolymer binder supported on a metallic current collector (not shown). The cathode 26 is typically a composite mixture of transitional metal oxide or phosphate and a polymer, copolymer or terpolymer binder including a lithium salt dissolved therein, supported by a current collector 28. The electrolyte 24 consists essentially of a lithium salt dissolved in a polymer, copolymer or terpolymer.

The cathode 26 preferably has a thickness of 70 µm±2 µm; the anode 22 preferably has a thickness of 50 µm±2 µm; and the electrolyte 24 preferably has a thickness of 40 µm±2 µm.

Figure 3:
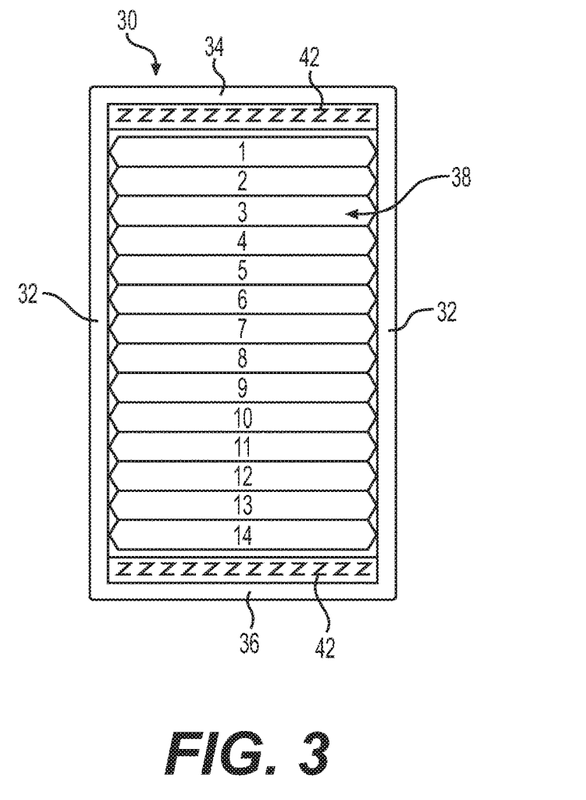
FIG. 3 is a schematic view of one embodiment of a battery having a bundle of electrochemical cells numbered 1 to 14 enclosed in a rigid casing.

Bundles of electrochemical cells 12 typically include a plurality of identical electrochemical cells 12 having the same number of laminates 20 and therefore having the same capacity. FIG. 3 illustrates schematically an embodiment of a battery having a single bundle 38 including 14 electrochemical cells 12 numbered 1 to 14 enclosed in a rigid casing 30 having side walls 32 and upper and lower walls 34 and 36. Each electrochemical cell 12 has the same number of laminates 20 and the same capacity.

Figure 4:
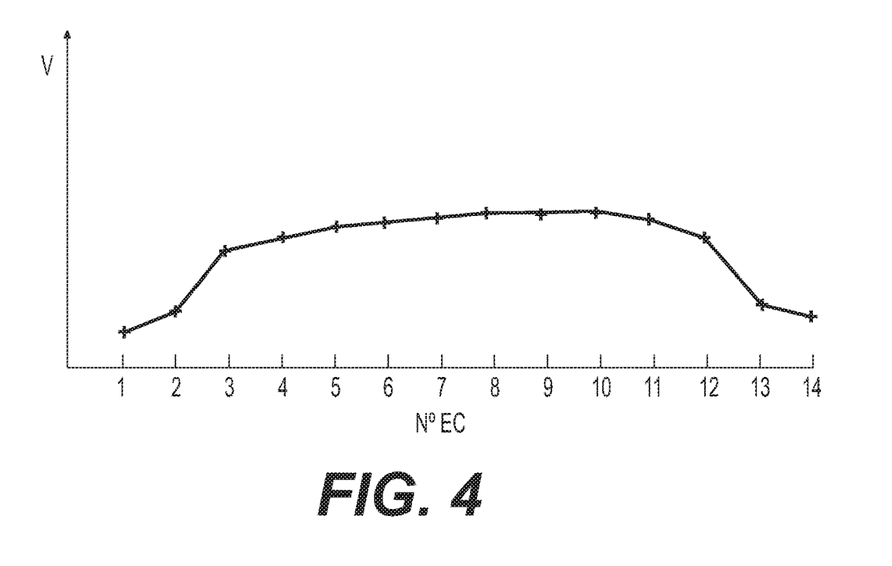
FIG. 4 is a graph of the voltage of each electrochemical cell numbered 1 to 14 at the end of a discharge of the battery shown in FIG. 3.

FIG. 4 is a graph showing the voltage of each electrochemical cell 12 numbered 1 to 14 at the end of a discharge of the battery. There emerges from the graph of FIG. 4 a profile indicating that electrochemical cells Nos. 1, 2 and 13, 14 have reached their end of discharge voltage more rapidly than electrochemical cells Nos. 3 to 12. Since the battery reaches its end of discharge voltage when one of the electrochemical cells 12 of the bundle 38 reaches its end of discharge, the battery stopped operating while a plurality of its electrochemical cells 12 were still within their voltage discharge operating window. The battery effectively stopped operating with capacity remaining.

Figure 5:
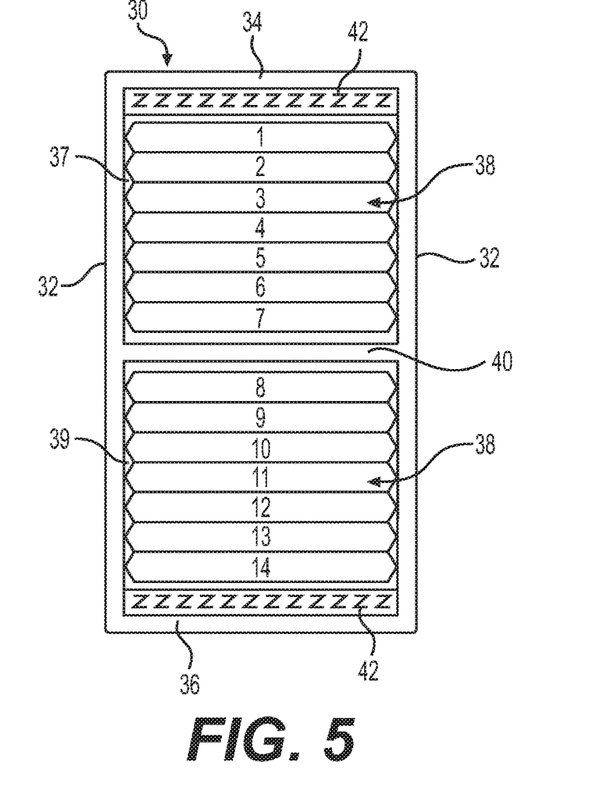
FIG. 5 is a schematic view of second embodiment of a battery having two bundles of electrochemical cells numbered 1 to 14 enclosed in a rigid casing.

FIG. 5 illustrates schematically an embodiment of a battery having two bundles 38 enclosed in a rigid casing 30 having side walls 32, upper and lower walls 34 and 36 and an internal wall 40 defining two enclosures 37 and 39. The first bundle 38 located in enclosure 37 includes 7 electrochemical cells 12 numbered 1 to 7 and the second bundle 38 located in enclosure 39 includes 7 electrochemical cells 12 numbered 8 to 14. As in the previous embodiment described with reference to FIG. 3, each electrochemical cell 12 of the two bundles 38 has the same number of laminates 20 and the same capacity.

Figure 6:
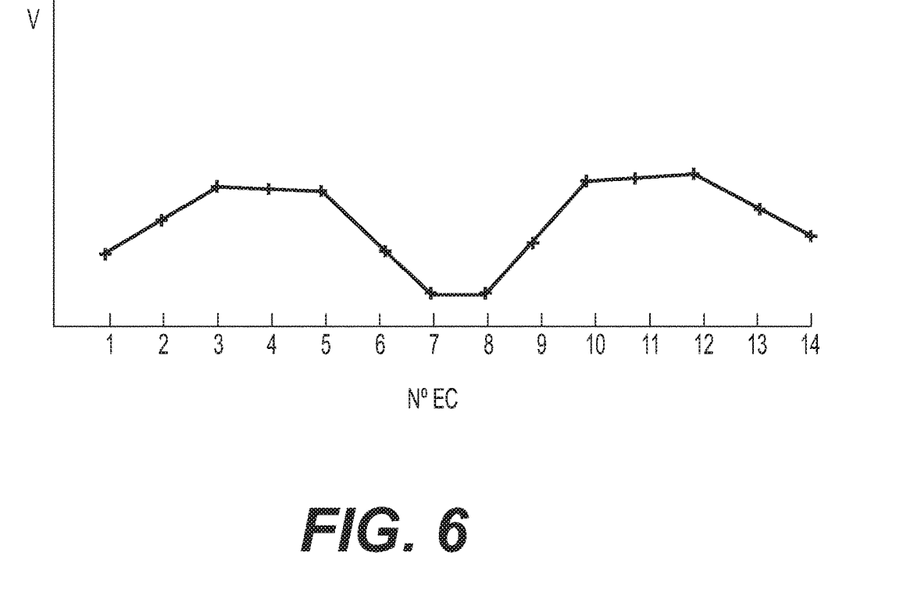
FIG. 6 is a graph of the voltage of each electrochemical cell numbered 1 to 14 at the end of a discharge of the battery shown in FIG. 5.

FIG. 6 is a graph showing the voltage of each electrochemical cell 12 numbered 1 to 7 and 8 to 14 at the end of a discharge of the battery. There emerges from the graph of FIG. 6 a profile indicating that electrochemical cells Nos. 1, 2, 6 to 9 and 13, 14 have reached their end of discharge voltage more rapidly than electrochemical cells Nos. 3 to 5 and 10 to 12. Since the battery reaches its end of discharge voltage when one of the electrochemical cells 12 of the bundle 38 reaches its end of discharge voltage, the battery stopped operating while a plurality of its electrochemical cells 12 were still within their voltage discharge operating window. Again, the battery effectively stopped operating with capacity remaining.

There emerges from the graphs of FIGS. 4 and 6 that the electrochemical cells located close to the heat sinks provided by the upper and lower walls 34 and 36 and by the internal wall 40 reach their end of discharge voltage more rapidly than the electrochemical cells located farther away from those heat sinks. Since the discharge capacity of the electrochemical cells 12 is dependent upon the temperature of the electrochemical cells 12, it stands to reason that the electrochemical cells located close to the heat sinks i.e. upper and lower walls 34 and 36 and/or internal wall 40, have more difficulties remaining at their operating temperatures due to their proximity to heat sinks and therefore are colder and effectively have less capacity than the electrochemical cells located farther away from the heat sinks.

To alleviate this problem, the inventors have tested a new bundle assembly in which the electrochemical cells close to the heat sinks provided by the upper and lower walls 34 and 36 and/or to the internal wall 40 have a different configuration than the electrochemical cells located farther away from the heat sinks.

In one embodiment, the electrochemical cells 12 close to the heat sinks have a higher capacity than the electrochemical cells located farther away from the heat sinks. To produce electrochemical cells 12 having a higher capacity, one solution is to increase the active surface of the electrochemical cell 12 by adding laminates 20 and effectively lowering the impedance or internal resistance of the electrochemical cell thereby increasing the capacity of the electrochemical cell 12.

Figure 7:
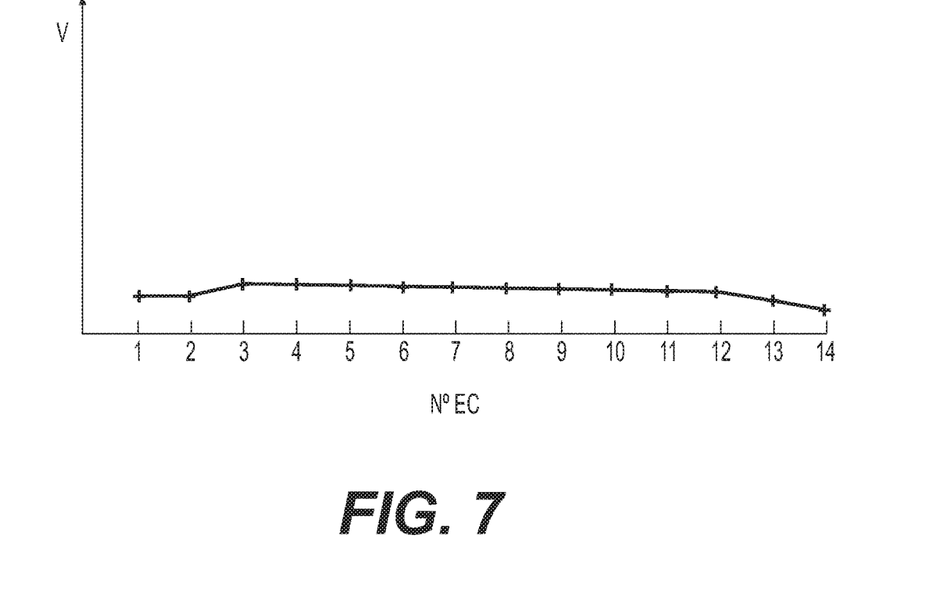
FIG. 7 is a graph showing the voltage of each electrochemical cell numbered 1 to 14 at the end of a discharge of the battery shown in FIG. 3 with a modified configuration.

Referring back to FIG. 3, a new bundle 38 was configured and assembled with electrochemical cells Nos. 3 to 12 having n laminates 20, electrochemical cells Nos. 2 and 13 having n+2 laminates 20 and electrochemical cells Nos. 1 and 14 having n+4 laminates 20. FIG. 7 is a graph showing the voltage of each electrochemical cell numbered 1 to 14 at the end of a discharge of the battery. The graph shows that the profile of end of discharge voltage of the electrochemical cells Nos. 1 to 14 has leveled off as compared to the profile of the graph of FIG. 4 and that electrochemical cells Nos. 1, 2 and 13, 14 have reached their end of discharge voltage almost at the same time as electrochemical cells Nos. 3 to 12.

Figure 8:
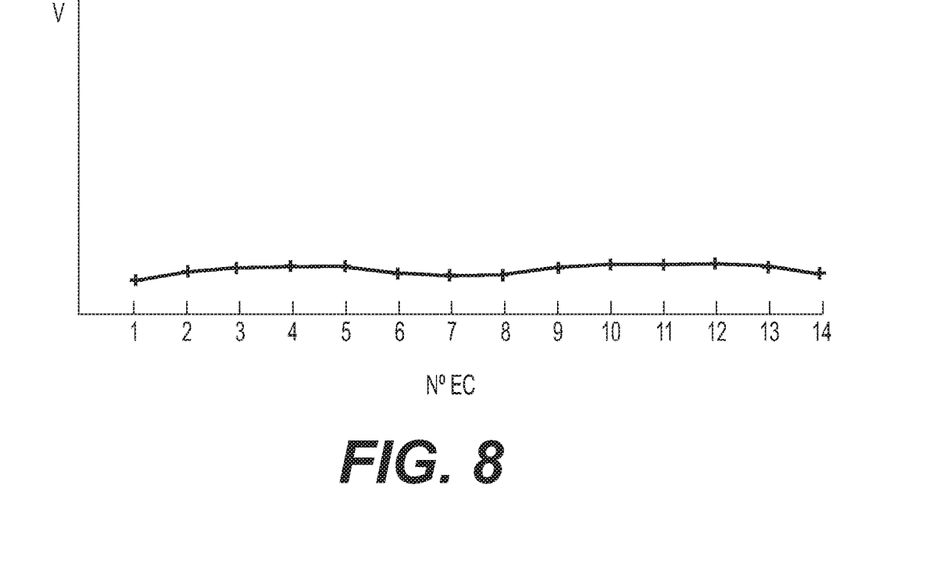
FIG. 8 is a graph showing the voltage of each electrochemical cell numbered 1 to 14 at the end of a discharge of the battery shown in FIG. 5 with a modified configuration.

Referring back to FIG. 5, similarly, two new bundles 38 were configured and assembled. The first bundle 38 was configured with electrochemical cells Nos. 3 to 5 having n laminates 20, electrochemical cells Nos. 2 and 6 having n+2 laminates 20 and electrochemical cells Nos. 1 and 7 having n+4 laminates 20. The second bundle 38 was configured with electrochemical cells Nos. 10 to 12 having n laminates 20, electrochemical cells Nos. 9 and 13 having n+2 laminates 20 and electrochemical cells Nos. 8 and 14 having n+4 laminates 20. FIG. 8 is a graph showing the voltage of each electrochemical cell numbered 1 to 14 at the end of a discharge of the battery. The graph shows that the profile of end of discharge voltage of the electrochemical cells Nos. 1 to 7 and 8 to 14 has leveled off as compared to the profile of the graph of FIG. 6 and that electrochemical cells Nos. 1, 2, 6-9 and 13, 14 have reached their end of discharge voltage almost at the same time as electrochemical cells Nos. 3 to 12.

Thus, the new configurations of bundle of electrochemical cells in which the electrochemical cells positioned adjacent or close to the heat sinks of the rigid casing i.e. upper and lower walls and internal wall of the rigid casing are more capacitive than the electrochemical cells of the bundle located farther away from the heat sinks solves the problem of premature end of discharge of the battery 10. The new configuration takes into account the position of the electrochemical cells relative to the various heat sinks of the rigid casing by increasing the capacity of the electrochemical cells close to the heat sinks and the increased capacity of the those electrochemical cells is obtained by adding laminates 20 to the electrochemical cells.

The more capacitive electrochemical cells 12 described have n+2 and n+4 laminates 20. However, various configurations of bundles 38 are possible depending on the measured differences of end of voltage of the electrochemical cells of a bundle 38. Configuration wherein the electrochemical cells 12 close to the heat sinks of the rigid casing have n+1, n+2, n+3, n+4 and n+5 are possible and contemplated.

Another solution to the problem of premature end of cycle of the electrochemical cells 12 located adjacent to the heat sinks provided by the upper and lower walls 34 and 36 and the internal wall 40, contemplated by the inventors was to lower the impedance or internal resistance of those electrochemical cells adjacent to the heat sinks by reducing the thickness of the cathodes 26 of each laminate 20.

In another specific embodiment, the impedance of the electrochemical cells 12 adjacent to the heat sinks is reduced by producing laminates 20 in which the cathode 26 is thinner than the cathode 26 of the laminates 20 of the other electrochemical cells 12. An electrochemical cell 12 in which each constituent laminate 20 is made with a cathode 26 having a thickness of 60 µm±2 µm instead of 70 µm±2 µm or approximately 10 µm less than the cathode of the laminates of the other electrochemical cells 12 of the bundle 38 will have a lower capacity than the other electrochemical cells but will perform better in discharge mode at lower temperature and this increased discharge capability should compensate for the lower temperature experienced by those electrochemical cells 12 close to the heat sinks. Preferably, the electrochemical cells 12 in which each constituent laminate 20 is made with a thinner cathode 26 should include more laminate 20 in order to compensate for the lower capacity.

The inventors have therefore tested a new bundle configuration in which the electrochemical cells 12 close to the heat sinks of the upper and lower walls 34 and 36 and/or to the internal wall 40 include laminates 20 made with a cathode 26 having a thickness of approximately 10 µm less than the cathode of the laminates of the other electrochemical cells 12 of the bundle 38 i.e a thickness of 60 µm±2 µm instead of 70 µm±2 µm. Referring back to FIG. 3, a new bundle 38 was configured and assembled with electrochemical cells Nos. 1 to 14 having n laminates 20 but with electrochemical cells Nos. 1, 2 and 13, 14 including laminates 20 made with a cathode 26 having a thickness of 60 µm±2 µm instead of 70 µm±2 µm.

Figure 9:
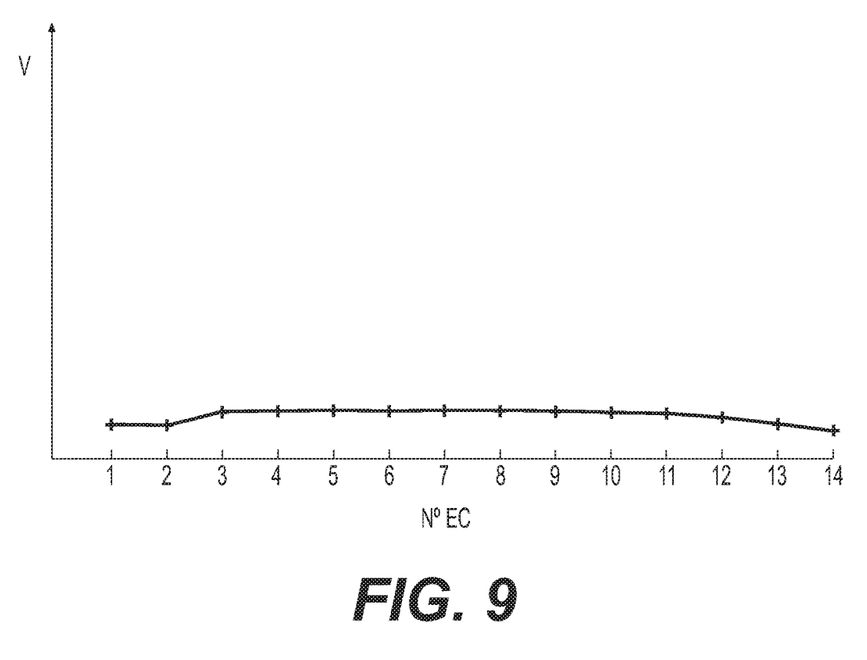
FIG. 9 is a graph showing the voltage of each electrochemical cell numbered 1 to 14 at the end of a discharge of the battery shown in FIG. 3 with a modified configuration.

FIG. 9 is a graph showing the voltage of each electrochemical cell numbered 1 to 14 at the end of a discharge of the battery. The graph shows that the profile of end of discharge voltage of the electrochemical cells Nos. 1 to 14 has leveled off as compared to the profile of the graph of FIG. 4 and that electrochemical cells Nos. 1, 2 and 13, 14 have reached their end of discharge voltage almost at the same time as electrochemical cells Nos. 3 to 12 which demonstrates that the increased discharge capability of electrochemical cells Nos. 1, 2 and 13, 14 at lower temperature has compensated for the lower temperature experienced by those electrochemical cells close to the heat sinks.

Referring back to FIG. 5, similarly, two new bundles 38 were configured and assembled. The first bundle 38 was configured and assembled with electrochemical cells Nos. 1 to 7 having n laminates 20 but with electrochemical cells Nos. 1, 2 and 6, 7 including laminates 20 made with a cathode 26 having a thickness of 60 µm±2 µm instead of 70 µm±2 µm or approximately 10 µm less than the cathode of the laminates of the other electrochemical cells of the bundle. The second bundle 38 was configured and assembled with electrochemical cells Nos. 8 to 14 having n laminates 20 but with electrochemical cells Nos. 8, 9 and 13, 14 including laminates 20 made with a cathode 26 having a thickness of 60 µm±2 µm instead of 70 µm±2 µm.

Figure 10:
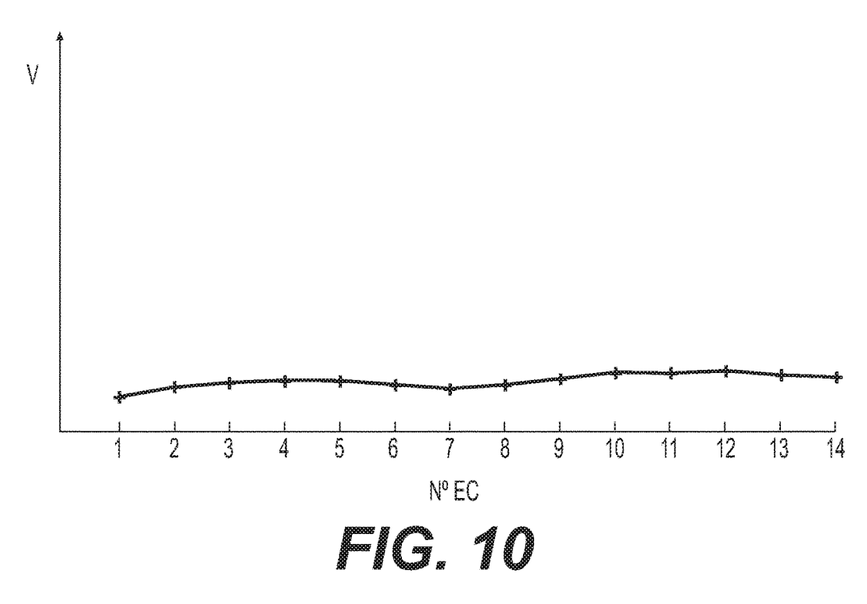
FIG. 10 is a graph showing the voltage of each electrochemical cell numbered 1 to 14 at the end of a discharge of the battery shown in FIG. 5 with a modified configuration.

FIG. 10 is a graph showing the voltage of each electrochemical cell numbered 1 to 14 at the end of a discharge of the battery. The graph shows that the profile of end of discharge voltage of the electrochemical cells Nos. 1 to 7 and 8 to 14 has leveled off as compared to the profile of the graph of FIG. 6 and that electrochemical cells Nos. 1, 2, 6-9 and 13, 14 have reached their end of discharge voltage almost at the same time as electrochemical cells Nos. 3 to 12 which further demonstrates that the increased discharge capability at lower temperature of the electrochemical cells close to the heat sinks has compensated for the lower temperature experienced by those electrochemical cells.

Figures 11, 12:
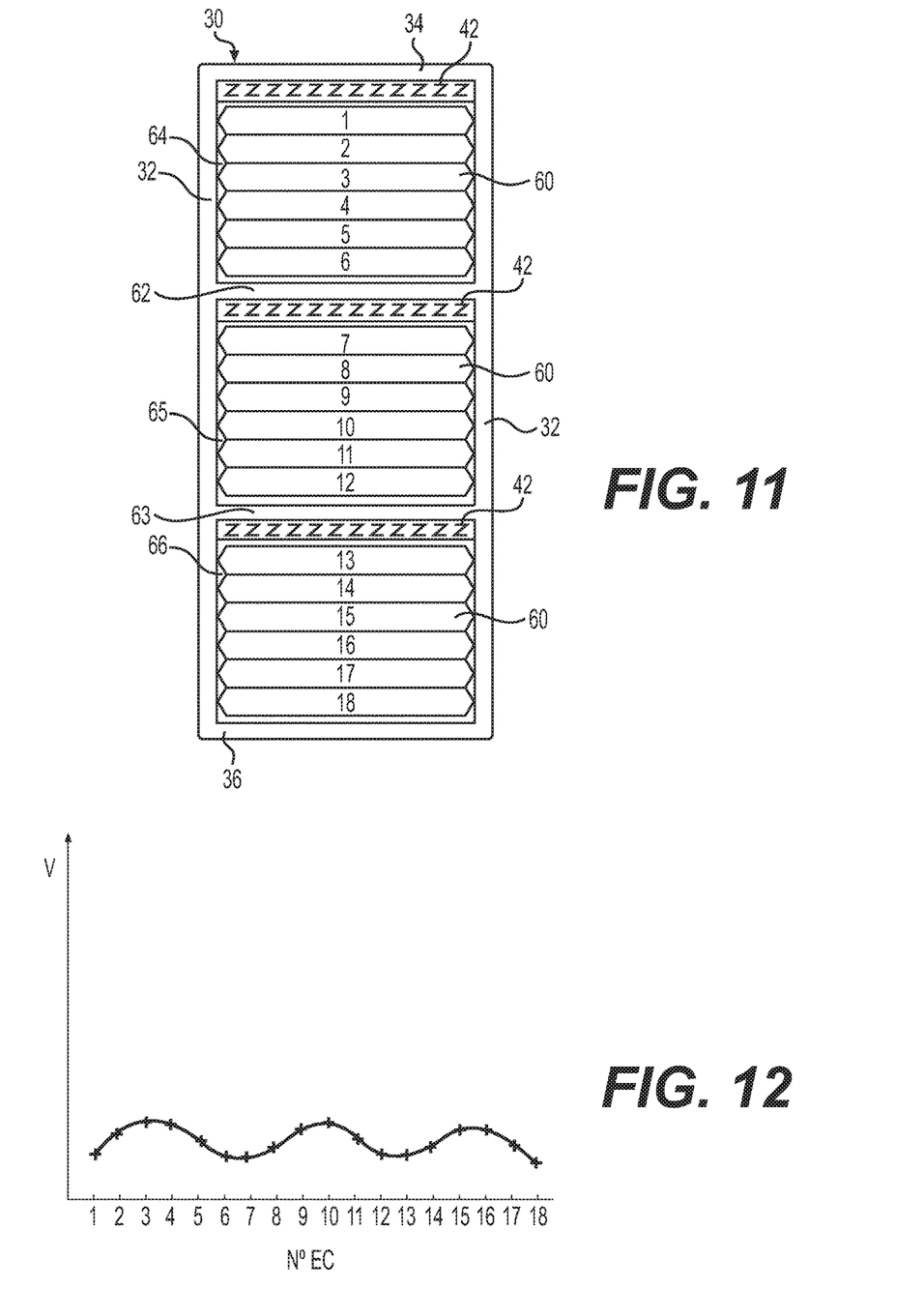
FIG. 11 is a schematic view of third embodiment of a battery having three bundles of electrochemical cells numbered 1 to 18 enclosed in a rigid casing.
FIG. 12 is a graph of the voltage of each electrochemical cell numbered 1 to 18 at the end of a discharge of the battery shown in FIG. 11.

FIG. 11 illustrates schematically another embodiment of a battery having three bundles 60 enclosed in a rigid casing 30 having side walls 32, upper and lower walls 34 and 36 and two internal walls 62 and 63 defining three enclosures 64, 65 and 66. The first bundle 60 located in enclosure 34 includes six electrochemical cells 12 numbered 1 to 6, the second bundle 60 located in enclosure 65 includes six electrochemical cells 12 numbered 7 to 12, and the third bundle 60 located in enclosure 66 includes six electrochemical cells 12 numbered 13 to 18. As in the previous embodiments described with reference to FIGS. 3 and 5, each electrochemical cell 12 of the two bundles 60 has the same number of laminates 20 and the same capacity.

FIG. 12 is a graph showing the voltage of each electrochemical cell 12 numbered 1 to 6, 7 to 12 and 13 to 18 at the end of a discharge of the battery. There emerges from the graph of FIG. 14 a profile indicating that electrochemical cells Nos. 1, 2, 5 to 8, 11 to 14 and 17, 18 have reached their end of discharge voltage more rapidly than electrochemical cells Nos. 3-4, 9-10, and 15-16. Since the battery reaches its end of discharge voltage when one of the electrochemical cells 12 of the bundle 38 reaches its end of discharge voltage to prevent overdischarge of its electrochemical cells 12, the battery stopped operating while a plurality of its electrochemical cells 12 were still within their voltage discharge operating window. Again, the battery effectively stopped operating with capacity remaining.

There emerges once again from the graph of FIG. 12 that the electrochemical cells located close to the heat sinks provided by the upper and lower walls 34 and 36 and by the internal walls 62 and 63 reach their end of discharge voltage more rapidly than the electrochemical cells located farther away from those heat sinks. Since the discharge capacity of the electrochemical cells 12 is dependent upon the temperature of the electrochemical cells 12, it stands to reason that the electrochemical cells located close to the heat sinks have more difficulties remaining at their operating temperatures due to their proximity to heat sinks and therefore are colder and effectively have less capacity than the electrochemical cells located farther away from the heat sinks.

The same solutions previously described apply to the embodiment of the battery of FIG. 11 including three bundles 60 enclosed in a rigid casing 30 having two internal walls 62 and 63 to alleviate this problem. The inventors have devised new bundle assemblies in which the electrochemical cells close to the heat sinks have a different configuration than the electrochemical cells located farther away from the heat sinks. Specifically, the electrochemical cells Nos. 1, 2, 5 to 8, 11 to 14 and 17, 18 which are close to the heat sinks may be configured to have a higher capacity than the electrochemical cells located farther away from the heat sinks by adding laminates 20 to the electrochemical cells Nos. 1, 2, 5 to 8, 11 to 14 and 17, 18 and effectively lowering the impedance or internal resistance of these electrochemical cells thereby increasing the capacity of electrochemical cell Nos. 1, 2, 5 to 8, 11 to 14 and 17, 18.

The other solution also applies to the embodiment of the battery of FIG. 11 including three bundles 60 wherein electrochemical cells Nos. 1, 2, 5 to 8, 11 to 14 and 17, 18 are made with laminates 20 having increased discharge capability at lower temperature of those electrochemical cells and lower impedance or internal resistance by reducing the thickness of the cathodes 26 as previously described.

The various solutions to the problem of premature end of cycle of the electrochemical cells located adjacent to the heat sinks provided by the walls of the casing of a battery also apply to a battery having plurality of cylindrical electrochemical cells or a plurality of prismatic electrochemical cells.

Figure 13A:
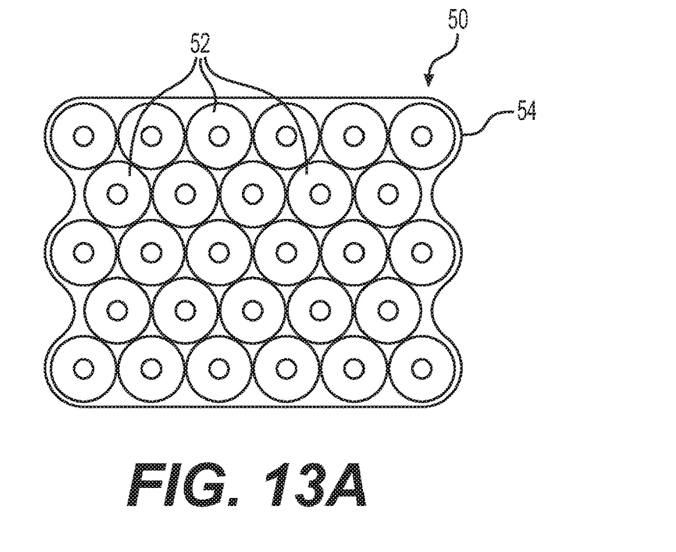
FIG. 13a is a schematic top plan view of another embodiment of a battery having a plurality of cylindrical electrochemical cells enclosed in a rigid casing.
Figure 13B:
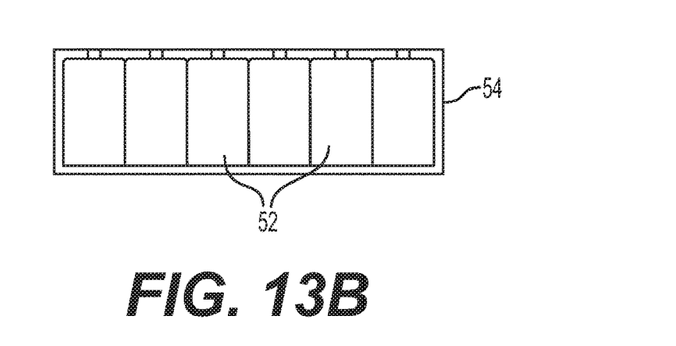
FIG. 13b is a schematic side elevational view of the battery shown in FIG. 13a having a plurality of cylindrical electrochemical cells enclosed in a rigid casing.

With reference to FIGS. 13*a* and 13*b*, there is shown a battery 50 including an array of cylindrical electrochemical cells 52 inserted in a rigid casing 54. The electrochemical cells 52 closest or adjacent to the walls of the rigid casing 54 which act as heat sinks are subject to the same problem of reaching the end of their discharge voltage before the electrochemical cells 52 located away from the heat sinks reach their end of discharge voltage. Because the battery 50 reaches its end of discharge voltage when one of the electrochemical cells 52 reaches its end of discharge voltage, the battery 50 stopped operating while a plurality of its electrochemical cells 52 were still within their voltage discharge operating window. The battery 50 therefore stopped operating with capacity remaining.

Figure 14:
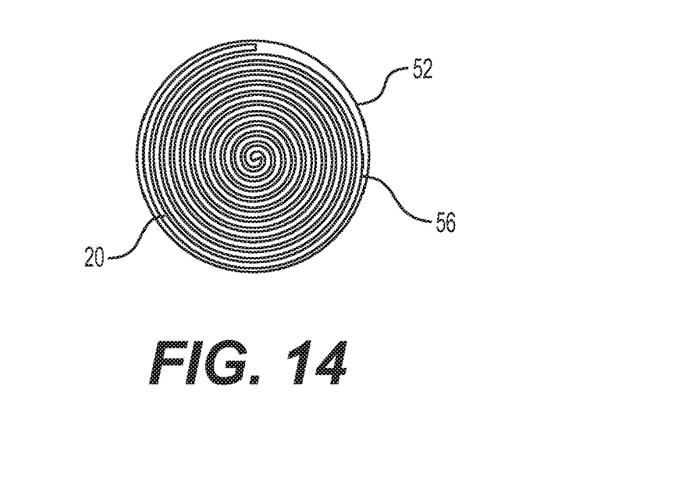
FIG. 14 is a schematic top plan view of a single cylindrical electrochemical cell.

With reference to FIG. 14, cylindrical electrochemical cells 52 consists of a single laminate 20 rolled multiple times into a spiral, the length of the single laminate 20 defines the number of layers or turns in the spiral roll 56 which defines the capacity of the cylindrical electrochemical cell 52. Therefore, in order to increase the capacity of the cylindrical electrochemical cells 52 close to or adjacent to the walls of the rigid casing 54, it is possible to produce cylindrical electrochemical cells 52 having a longer laminate 20 rolled into a spiral and therefore produce an electrochemical cell 52 having one or more layers or turns in the spiral roll 56. As previously described, positioning cylindrical electrochemical cells 52 having more capacity adjacent to the walls of the rigid casing 54 which act as heat sinks solves the problem of reaching the end of their discharge voltage before the electrochemical cells 52 located away from the heat sinks reach their end of discharge voltage. As well, producing an electrochemical cell 52 having a laminate 20 in which the cathode 26 is thinner than the cathode 26 of the laminate 20 of the other electrochemical cells 52 will reduce the impedance of the electrochemical cells 52 adjacent to the heat sinks which will perform better in discharge mode at lower temperature and this increased discharge capability will compensate for the lower temperature experienced by those electrochemical cells 52 close to the heat sinks and furthermore the laminate 20 having a thinner cathode 26 will be thinner such that the spiral roll 56 will include more layers or turns thereby compensating for the lower capacity of a thinner cathode 26.

Similarly, a battery which includes a plurality of prismatic electrochemical cells inserted in a rigid casing will encounter the same problem wherein the prismatic electrochemical cells closest or adjacent to the walls of the rigid casing which act as heat sinks will reach the end of their discharge voltage before the electrochemical cells located away from the heat sinks reach their end of discharge voltage and therefore the battery will reach its end of discharge voltage when one of the electrochemical cells reaches its end of discharge voltage. The battery will stop operating while a plurality of its prismatic electrochemical cells is still within their voltage discharge operating window. The prismatic battery therefore stopped operating with capacity remaining.

As described with reference to cylindrical electrochemical cells 52, a prismatic electrochemical cell consists of a single laminate flat rolled multiple times into a flat spiral roll; the length of the single laminate defines the number of layers or turns in the flat spiral roll which defines the capacity of the prismatic electrochemical cell. Therefore, to increase the capacity of the prismatic electrochemical cell close to or adjacent to the walls of the rigid casing, it is possible to produce prismatic electrochemical cells having a longer laminate rolled into a flat spiral roll and therefore produce a an electrochemical cell having one or more layers or turns in the flat spiral roll. As previously described, positioning prismatic electrochemical cells having more capacity adjacent to the walls of the rigid casing which act as heat sinks solves the problem of reaching the end of their discharge voltage before the prismatic electrochemical cells located away from the heat sinks reach their end of discharge voltage. As well, producing prismatic electrochemical cells with a laminate having a thinner cathode rolled into a flat spiral roll will have a lower impedance and more layers or turns in the flat spiral roll thereby increasing the discharge capability of the electrochemical call at lower temperature.

The same problematic applies to batteries using cooling systems to maintain the temperature of their electrochemical cells below a predetermined temperature threshold. The electrochemical cells located closest to the path of the cooling fluid which acts as heat sinks will reach their end of their discharge voltage before the electrochemical cells located away from the heat sinks. As described with reference to the previous embodiments of the invention, the problem is solved by rearranging the electrochemical cells in the battery such that the electrochemical cells positioned adjacent to the heat sink path of the cooling system have a different configuration than the other electrochemical cells of the battery.

Modifications and improvements to the above-described embodiments of the present invention may become apparent to those skilled in the art. The foregoing description is intended to be exemplary rather than limiting. The scope of the present invention is therefore intended to be limited solely by the scope of the appended claims.

What is claimed is:

1. A lithium battery comprising:
   a plurality of electrochemical cells assembled together, the plurality of electrochemical cells including:
      at least one first electrochemical cell;
      at least one second electrochemical cell; and
      at least one third electrochemical cell disposed between the at least one first electrochemical cell and the at least one second electrochemical cell; and
   a rigid casing having a plurality of walls forming an enclosure, the plurality of walls including a first wall and a second wall, the second wall being disposed opposite the first wall,
   the at least one first electrochemical cell being disposed between the first wall and the at least one third electrochemical cell,
   the at least one second electrochemical cell being disposed between the second wall and the at least one third electrochemical cell,
   the first and second walls providing a heat sink path to dissipate excess heat generated by the plurality of electrochemical cells,
   the at least one first electrochemical cell being more capacitive than the at least one third electrochemical cell, and
   the at least one second electrochemical cell being more capacitive than the at least one third electrochemical cell.

2. A lithium battery as defined in claim 1, wherein:
   the at least one third electrochemical cell includes n laminates; and
   the at least one first electrochemical cell and the at least one second electrochemical cell each include at least n+1 laminates.

3. A lithium battery as defined in claim 2, wherein the at least one first electrochemical cell and the at least one second electrochemical cell each include at least n+2 laminates.

4. A lithium battery as defined in claim 1, wherein:
   the plurality of walls includes an internal wall providing a further heat sink path;
   the plurality of electrochemical cells further includes:
      at least one fourth electrochemical cell;
      at least one fifth electrochemical cell being disposed between the at least one third electrochemical cell and the internal wall, the at least one third electrochemical cell being disposed between the at least one first electrochemical cell and the at least one fifth electrochemical cell; and
      at least one sixth electrochemical cell being disposed between the at least one fourth electrochemical cell and the internal wall, the at least one fourth electrochemical cell being disposed between the at least one second electrochemical cell and the at least one sixth electrochemical cell;
   the at least one second electrochemical cell being more capacitive than the at least one fourth electrochemical cell, the at least one fifth electrochemical cell being more capacitive than the at least one third electrochemical cell, and the at least one sixth electrochemical cell being more capacitive than the at least one fourth cell.

5. A lithium battery as defined in claim 4, wherein:
the at least one third electrochemical cell and the at least one fourth electrochemical cell each include n laminates; and
the at least one first electrochemical cell, the at least one second electrochemical cell, the at least one fifth electrochemical cell and the at least one sixth electrochemical cell each include at least n+1 laminates.

6. A lithium battery as defined in claim 5, wherein the at least one first electrochemical cell, the at least one second electrochemical cell, the at least one fifth electrochemical cell and the at least one sixth electrochemical cell each include at least n+2 laminates.

7. A lithium battery as defined in claim 1, wherein the at least one first electrochemical cell and the at least one second electrochemical cell each have a lower impedance than the at least one third electrochemical cell.

8. A lithium battery as defined in claim 7, wherein:
each electrochemical cell of the plurality of electrochemical cells includes an anode, a cathode and an electrolyte; and
the cathode of the at least one first electrochemical cell and the cathode of the at least one second electrochemical cell are thinner than the cathode of the at least one third electrochemical cell.

9. A lithium battery as defined in claim 8, wherein the cathode of the at least one first electrochemical cell and the cathode of the at least one second electrochemical cell have a thickness of approximately 10 µm less than the cathode of the at least one third electrochemical cell.

10. A lithium battery as defined in claim 1, wherein:
each electrochemical cell of the plurality of electrochemical cells consists of a multi-layer assembly of single laminates; and
the electrochemical cells of the plurality of electrochemical cells are stacked one against the other to form a bundle.

11. A lithium battery as defined in claim 1, wherein each electrochemical cell of the plurality of electrochemical cells consists of a single laminate rolled multiple times into a spiral to form a cylindrical electrochemical cell.

12. A lithium battery as defined in claim 1, further comprising a pressure system disposed between the first wall and the at least one first electrochemical cell.

13. A lithium battery as defined in claim 12, wherein the pressure system includes:
a plate; and
a series of springs disposed between the first wall and the plate.

14. A lithium battery as defined in claim 1, wherein:
one of the at least one first electrochemical cell is the electrochemical cell of the plurality of electrochemical cells which is closest to the first wall; and
one of the at least one second electrochemical cell is the electrochemical cell of the plurality of electrochemical cells which is closest to the second wall.

15. A lithium battery as defined in claim 4, wherein:
one of the at least one fifth electrochemical cell is adjacent to the internal wall; and
one of the at least one sixth electrochemical cell is adjacent to the internal wall.

* * * * *